(12) United States Patent
Thornton

(10) Patent No.: US 8,671,946 B2
(45) Date of Patent: Mar. 18, 2014

(54) CUSTOM DENTAL APPLIANCE AND METHOD OF CREATING A CUSTOM DENTAL APPLIANCE

(75) Inventor: W. Keith Thornton, Dallas, TX (US)

(73) Assignee: Airway Technologies, LLC, Carrollton, TX (US)

( * ) Notice: Subject to any disclaimer, the term of this patent is extended or adjusted under 35 U.S.C. 154(b) by 296 days.

(21) Appl. No.: 13/080,050

(22) Filed: Apr. 5, 2011

(65) Prior Publication Data

US 2012/0255559 A1 Oct. 11, 2012

(51) Int. Cl.
*A61F 5/56* (2006.01)

(52) U.S. Cl.
USPC ............................................ 128/848; 602/902

(58) Field of Classification Search
USPC .......... 128/848, 859, 860, 861, 862; 602/902; 433/6
See application file for complete search history.

(56) References Cited

U.S. PATENT DOCUMENTS

| | | |
|---|---|---|
| 690,663 A | 1/1902 | Pratt |
| 746,869 A | 12/1903 | Moulton |
| 774,446 A | 11/1904 | Moulton |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,424,533 A | 7/1947 | Faires |
| 2,505,028 A | 4/1950 | Boeger |

(Continued)

FOREIGN PATENT DOCUMENTS

| | | |
|---|---|---|
| DE | 2 320 501 | 11/1974 |
| DE | 2320501 | 11/1974 |

(Continued)

OTHER PUBLICATIONS

PCT Notification of Transmittal of the International Search Report and the Written Opinion of the International Searching Authority, or the Declaration; mailed Jul. 17, 2012; International app No. PCT/US2012/028885; 18 pages.

(Continued)

*Primary Examiner* — Justine R Yu
*Assistant Examiner* — Raymond E Harris
(74) *Attorney, Agent, or Firm* — Baker Botts L.L.P.

(57) ABSTRACT

According to one embodiment, a dental device is provided. The dental device includes an arched frame configured to be positioned proximate to the occlusal surface of a user's dental arch such that the arched frame extends beyond the cuspids of the user's dental arch. The arched frame defines a plurality of apertures, and the arched frame includes an adjustment mechanism. The dental device further includes a moldable tray coupled to the arched frame. The moldable tray engages the plurality of apertures and includes a channel configured to engage at least some of the teeth of the user's dental arch.

18 Claims, 11 Drawing Sheets

(56) References Cited

U.S. PATENT DOCUMENTS

| | | |
|---|---|---|
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,833,278 A | 5/1958 | Ross |
| 2,867,212 A | 1/1959 | Nunn, Jr. |
| 2,882,893 A | 4/1959 | Godfroy |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick et al. |
| 3,522,805 A | 8/1970 | Wallshein |
| 3,690,004 A | 9/1972 | Frush |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner et al. |
| 4,026,024 A | 5/1977 | Tradowsky |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud et al. |
| 4,258,710 A | 3/1981 | Reber |
| 4,289,127 A | 9/1981 | Nelson |
| 4,304,227 A | 12/1981 | Samelson |
| 4,376,628 A | 3/1983 | Aardse |
| 4,382,783 A | 5/1983 | Rosenberg |
| 4,419,992 A | 12/1983 | Chorbajian |
| 4,433,956 A | 2/1984 | Witzig |
| 4,439,147 A | 3/1984 | Magill et al. |
| 4,439,149 A | 3/1984 | Devincenzo |
| 4,454,090 A | 6/1984 | Saumell |
| 4,495,945 A | 1/1985 | Liegner |
| 4,505,672 A | 3/1985 | Kurz |
| 4,530,662 A | 7/1985 | Andersson et al. |
| 4,553,549 A | 11/1985 | Pope et al. |
| 4,568,280 A | 2/1986 | Ahlin |
| 4,569,342 A | 2/1986 | von Nostitz |
| 4,593,686 A | 6/1986 | Lloyd et al. |
| 4,602,905 A | 7/1986 | O'Keefe, III |
| 4,639,220 A | 1/1987 | Nara et al. |
| 4,668,188 A | 5/1987 | Wolfenson et al. |
| 4,669,459 A | 6/1987 | Spiewak et al. |
| 4,676,240 A | 6/1987 | Gardy |
| 4,715,368 A | 12/1987 | George |
| 4,741,696 A | 5/1988 | Cetlin |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,862,903 A | 9/1989 | Campbell |
| 4,892,478 A | 1/1990 | Tateosian et al. |
| 4,901,737 A | 2/1990 | Toone |
| 4,932,867 A | 6/1990 | Ueno |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman et al. |
| 5,028,232 A | 7/1991 | Snow |
| 5,040,976 A | 8/1991 | Ubel, III et al. |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte et al. |
| 5,056,534 A | 10/1991 | Wright |
| 5,064,371 A | 11/1991 | Smeltzer |
| 5,066,231 A | 11/1991 | Oxman et al. |
| 5,078,600 A | 1/1992 | Austin |
| 5,082,007 A * | 1/1992 | Adell ............................ 128/861 |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| 5,154,184 A | 10/1992 | Alvarez |
| 5,154,609 A | 10/1992 | George |
| 5,183,057 A | 2/1993 | Syrop et al. |
| 5,188,529 A | 2/1993 | Lüth |
| 5,190,457 A | 3/1993 | Schreinemakers |
| 5,213,498 A | 5/1993 | Pelerin |
| 5,265,595 A | 11/1993 | Rudolph |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen et al. |
| 5,365,945 A | 11/1994 | Halstrom |
| 5,370,533 A | 12/1994 | Bushnell |
| 5,373,859 A | 12/1994 | Forney |
| 5,409,017 A | 4/1995 | Lowe |
| 5,415,544 A | 5/1995 | Oxman et al. |
| 5,427,117 A | 6/1995 | Thornton |
| 5,474,060 A | 12/1995 | Evans |
| 5,499,633 A | 3/1996 | Fenton |
| 5,503,552 A | 4/1996 | Diesso |
| 5,537,994 A | 7/1996 | Thornton |
| 5,551,872 A | 9/1996 | Mena |
| 5,562,449 A | 10/1996 | Jacobs et al. |
| 5,566,683 A | 10/1996 | Thornton |
| 5,570,704 A | 11/1996 | Buzzard et al. |
| 5,582,517 A | 12/1996 | Adell |
| 5,678,567 A | 10/1997 | Thornton et al. |
| 5,681,164 A | 10/1997 | Bass |
| 5,718,244 A | 2/1998 | Thornton |
| 5,720,302 A | 2/1998 | Belfer |
| 5,755,219 A | 5/1998 | Thornton |
| 5,807,100 A | 9/1998 | Thornton |
| 5,829,441 A * | 11/1998 | Kidd et al. .................... 128/848 |
| 5,846,082 A | 12/1998 | Thornton |
| 5,891,372 A | 4/1999 | Besset et al. |
| 5,954,048 A | 9/1999 | Thornton |
| 5,983,892 A | 11/1999 | Thornton |
| 6,012,919 A | 1/2000 | Cross, III |
| 6,083,442 A | 7/2000 | Gabilly |
| 6,109,265 A | 8/2000 | Frantz et al. |
| 6,155,262 A | 12/2000 | Thornton et al. |
| 6,209,542 B1 | 4/2001 | Thornton |
| 6,247,926 B1 | 6/2001 | Thornton |
| 6,305,376 B1 | 10/2001 | Thornton |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,450,167 B1 | 9/2002 | David et al. |
| 6,464,924 B1 | 10/2002 | Thornton |
| 6,516,805 B1 | 2/2003 | Thornton |
| 6,536,439 B1 | 3/2003 | Palmisano |
| 6,571,798 B1 | 6/2003 | Thornton |
| 6,604,527 B1 | 8/2003 | Palmisano |
| 6,675,802 B1 | 1/2004 | Thornton |
| 6,758,212 B2 | 7/2004 | Swann |
| 6,845,774 B2 * | 1/2005 | Gaskell ........................ 128/848 |
| 6,877,513 B2 | 4/2005 | Scarberry et al. |
| 7,174,895 B2 * | 2/2007 | Thornton et al. ............. 128/848 |
| 7,597,103 B2 * | 10/2009 | Thornton et al. ............. 128/848 |
| 7,650,885 B2 | 1/2010 | Paoluccio et al. |
| 7,677,889 B2 | 3/2010 | Thornton |
| 7,721,741 B2 | 5/2010 | Thornton |

(56) References Cited

U.S. PATENT DOCUMENTS

| | | | |
|---|---|---|---|
| 7,748,386 | B2 | 7/2010 | Thornton |
| 7,823,590 | B2 | 11/2010 | Bibi et al. |
| 7,832,403 | B2 | 11/2010 | Halstrom |
| 7,909,035 | B2 | 3/2011 | Thornton |
| 8,020,276 | B2 | 9/2011 | Thornton |
| 2002/0000230 | A1 | 1/2002 | Gaskell |
| 2002/0139366 | A1 | 10/2002 | Gaschke |
| 2003/0217753 | A1 | 11/2003 | Thornton |
| 2003/0234022 | A1* | 12/2003 | Belfer ............... 128/861 |
| 2004/0079374 | A1 | 4/2004 | Thornton |
| 2004/0226563 | A1 | 11/2004 | Xu et al. |
| 2004/0237965 | A1 | 12/2004 | Bibi et al. |
| 2005/0028827 | A1 | 2/2005 | Halstrom |
| 2005/0034733 | A1 | 2/2005 | Liddle et al. |
| 2005/0268914 | A1 | 12/2005 | Paoluccio et al. |
| 2007/0125388 | A1 | 6/2007 | Thornton et al. |
| 2007/0209666 | A1* | 9/2007 | Halstrom et al. ......... 128/859 |
| 2007/0235037 | A1 | 10/2007 | Thornton |
| 2008/0006273 | A1 | 1/2008 | Thornton |
| 2008/0006274 | A1 | 1/2008 | Thornton |
| 2008/0032256 | A1 | 2/2008 | Thornton |
| 2008/0060648 | A1 | 3/2008 | Thornton et al. |
| 2008/0127984 | A1 | 6/2008 | Thornton |
| 2008/0295850 | A1 | 12/2008 | Lesniak |
| 2009/0130624 | A1 | 5/2009 | Sun et al. |
| 2009/0272387 | A1* | 11/2009 | Spencer ............... 128/848 |
| 2010/0065067 | A1 | 3/2010 | Lee |
| 2011/0168187 | A1 | 7/2011 | Nelissen |

FOREIGN PATENT DOCUMENTS

| | | |
|---|---|---|
| DE | 3719009 | 12/1988 |
| DE | 29506512 | 7/1995 |
| DE | 29506512.5 | 7/1995 |
| EP | 0 312 368 A1 | 4/1989 |
| EP | 0312368 | 4/1989 |
| EP | 0 359 135 A1 | 3/1990 |
| EP | 0359135 | 3/1990 |
| GB | 1 569 129 | 6/1980 |
| GB | 1569129 | 6/1980 |
| GB | 2 072 567 A | 10/1981 |
| GB | 2072567 | 10/1981 |
| WO | WO 91/12777 | 9/1991 |
| WO | WO 97/25010 | 7/1997 |
| WO | WO 98/26736 | 6/1998 |
| WO | WO 98/46177 | 10/1998 |

OTHER PUBLICATIONS

Craig, William H., et al.; "Skeletal class II treatment with the Chateau appliance," The Journal of Pedondontics (vol. 11:120); pp. 120-138, 1987.

Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages.

Mayo Clinic Health Letter; Reliable Information for a Healthier Life; *Snoring: Laser Surgery Joins Battle to Restore Peace and Quiet*; vol. 13, No. 7, 8 pages, Jul. 1995.

Photocopies of 2-piece dental device manufactured by Currie-Gibson Dental Laboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 3 pages.

Great Lakes Orthodontics, Ltd.; *Nocturnal Airway Patency Applicance*; 2 pages.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WPI, Section PQ, Week 9039, Derwent Publications, Ltd., London, GB; XP-002116355 Abstract—Surgical Mouth Air Duct; 1 page, Dec. 15, 1989.

Personally Moulded Sleep Apnea Masks, http://;web.archive.org/web/20030618145716/ www.sleepapneamasks.com.au/default.asp, downloaded Aug. 17, 2009 (2 pages).

European Patent Office, Application No. 03 809 555.0-125, Applicant: W. Keith Thornton, 3 pages, dated Feb. 23, 2010; 4 pages.

PCT Notification of Transmittal of the International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

PCT, Notification of Transmittal of the International Search Report and the Written Opinion of the International Searching Authority, or the Declaration, PCT/US07/02736, 10 pages, Date Mailed: Oct. 26, 2007.

PCT, Notification of Transmittal of the International Search Report and the Written Opinion of the International Searching Authority, or the Declaration, International Application No. PCT/US2011/039231, filed Jun. 6, 2011 (11 pgs).

PCT, Notification of Transmittal of the International Search Report and the Written Opinion of the International Searching Authority, or the Declaration, PCT/US2010/051136, 10 pages, Mar. 4, 2011.

PCT Intl. Searching Authority, Invitation to pay Add'l Fees, Re PCT/US2012/032407 mailed May 30, 2012.

Japanese Patent Office re patent application 2004-500750, mailed Oct. 14, 2008.

Australian Office Action re patent application No. 2007/243957 dated Mar. 9, 2012.

Canadian IPO patent application No. 2,502,280 dated Feb. 23, 2010.

PCT Intl. Searching Authority, Invitation to pay Add'l Fees, Re PCT/US2012/028885 mailed May 30, 2012 (0306 Foreign).

PCT Intl. Searching Authority, Invitation to pay Add'l Fees, Re PCT/US2012/032407 mailed May 30, 2012 (0314 Foreign).

PCT Intl. Search Report and Written Opinion, PCT/US06/26622, 11 pgs.

Japanese PO Action re Japanese Appln No. 2004-500750, 4 pages, mailed Oct. 14, 2008.

Photocopies of 2-piece dental device manufactured by Currie-Gibson Dental Lboratory, Inc., prior to Apr. 13, 1993, 5 pages.

Database WOI, Section PQ, Week 9039, Derwent Publications, Ltd., London, GB; XP-002116355 Abstract—*Surgical Mouth Air Duct*; 1 pages, Dec. 15, 1989.

PCT Notification of Transmittal of the International Search Report and the Written Opinion of the International Searching Authority, or the Declaration; mailed Jul. 13, 2012; International app No. PCT/US2012/032407; 18 pages.

* cited by examiner

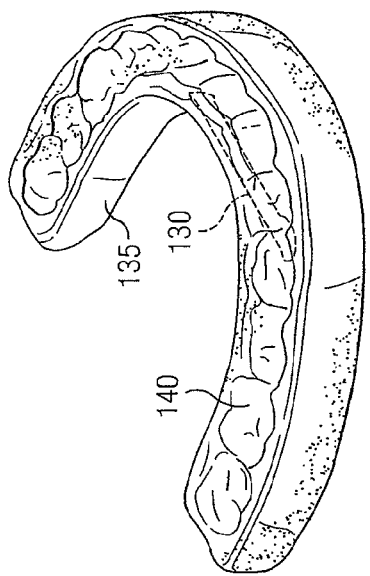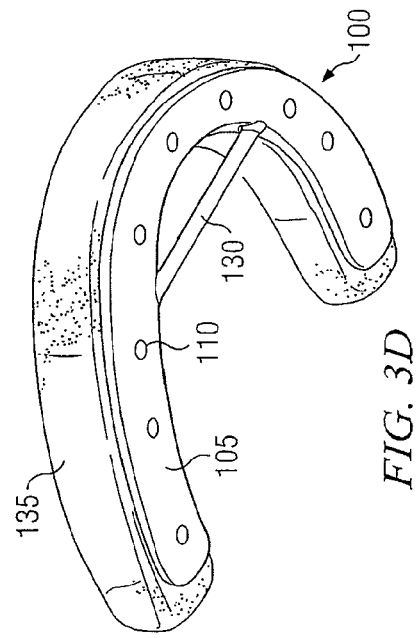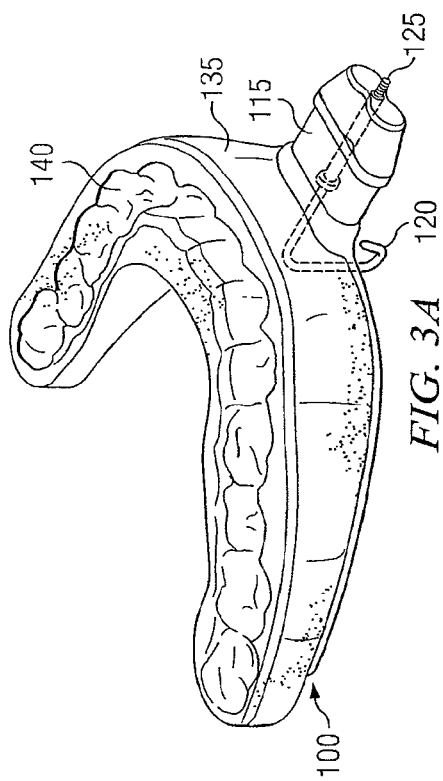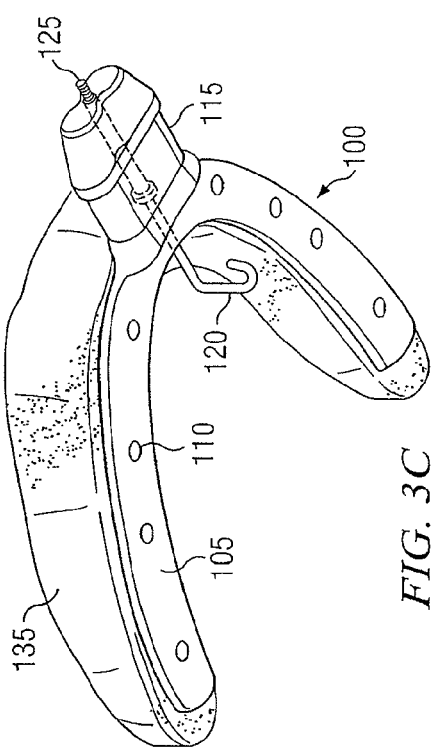

US 8,671,946 B2

CUSTOM DENTAL APPLIANCE AND METHOD OF CREATING A CUSTOM DENTAL APPLIANCE

TECHNICAL FIELD OF THE INVENTION

This invention relates generally to medical and dental devices, and more particularly to a custom dental appliance with a moldable tray configured to engage a particular user's teeth.

BACKGROUND

Many people experience difficulty in sleeping because of breathing problems. These problems may result in snoring, or the more serious condition of sleep apnea. One treatment for sleep breathing disorders involves the use of dental devices for extending forward the lower jaw of the patient. These devices operate to more fully open the breathing passageway, thereby allowing for easier breathing, whether that breathing be through the nose or through the mouth. Furthermore, many people suffer from degraded teeth or jaw pain arising from bruxing or the grinding of teeth during sleep. One treatment for grinding involves the use of dental devices that put pressure on a patient's front teeth to relax and unclench the patient's jaw.

These dental devices may be created in labs after a dentist sends in a patient's dental impressions. This procedure can cost the patient substantial time and money because the dentist creates a dental impression and then the lab creates the dental device after the dentist sends in the dental impression. Also, these lab-created dental devices are often designed to target particular problems. For example, a device for treating snoring may not help a patient who grinds his teeth.

People who suffer from sleep problems may seek help from a sleep laboratory. Doctors at the laboratory may perform tests on patients as they sleep. Doctors may further test the effectiveness of various dental devices on the patients as treatment options. During tests, doctors may need quick access inside a patient's mouth, and dental devices that hook or attach inside the patient's mouth may hinder the doctors' ability to gain quick access inside the mouth. This scenario may also occur during surgery when a patient is unconscious, and a dental device is inserted into the mouth to maintain the patient's airway.

SUMMARY OF THE INVENTION

In accordance with the teachings of the present invention, a dental device is provided which may reduce or eliminate disadvantages and problems associated with prior art devices.

In one embodiment, a dental device is provided comprising an arched frame and a moldable tray. The arched frame may be configured to be positioned proximate to the occlusal surface of a user's dental arch such that the arched frame extends beyond the cuspids of the user's dental arch. The arched frame may define a plurality of apertures and may comprise an adjustment mechanism. The moldable tray may be coupled to the arched frame and may engage the plurality of apertures. The moldable tray may comprise a channel configured to engage at least some of the teeth of the user's dental arch.

In a particular embodiment, a dental device is provided comprising an arched frame, a moldable tray, a second arched frame, and a second moldable tray. The arched frame may be configured to be positioned proximate to the occlusal surface of a user's maxillary arch such that the arched frame extends beyond the cuspids of the user's maxillary arch. The arched frame may define a plurality of apertures and may comprise an adjustment mechanism. The adjustment mechanism may comprise a hook and a threaded adjustor. The moldable tray may be coupled to the arched frame and may engage the plurality of apertures. The moldable tray may comprise a channel configured to engage at least some of the teeth of the user's maxillary arch. The second arched frame may be configured to be positioned proximate to the occlusal surface of a user's mandibular arch such that the second arched frame extends beyond the cuspids of the user's mandibular arch. The second arched frame may define a second plurality of apertures and may comprise a receiving mechanism coupled to the lingual portion of the lower arched body. The second moldable tray may be coupled to the second arched frame and may engage the plurality of apertures. The second moldable tray may comprise a second channel configured to engage at least some of the teeth of the user's mandibular arch. The hook may engage the receiving mechanism, and the threaded adjustor may adjust the forward position of the arched frame relative to the second arched frame.

In another embodiment, a dental device may include an arched frame configured to be positioned proximate to the occlusal surface of a user's dental arch such that the arched frame extends beyond the cuspids of the user's dental arch. The arched frame may define a plurality of apertures. The dental device may further include an adjustment mechanism coupled to the arched frame. The dental device may further include a moldable tray coupled to the arched frame. The moldable tray may engage the plurality of apertures and may comprise a channel configured to engage at least some of the teeth of the user's dental arch.

In another embodiment, a dental device may include an arched frame configured to be positioned proximate to the occlusal surface of a user's maxillary arch such that the arched frame extends beyond the cuspids of the user's maxillary arch. The arched frame may define a plurality of apertures. The dental device may further include an adjustment mechanism coupled to the arched frame. The adjustment mechanism may comprise a hook and a threaded adjustor. The dental device may further include a moldable tray coupled to the arched frame. The moldable tray may engage the plurality of apertures and may comprise a channel configured to engage at least some of the teeth of the user's maxillary arch. The dental device may further include a second arched frame configured to be positioned proximate to the occlusal surface of a user's mandibular arch such that the arched frame extends beyond the cuspids of the user's mandibular arch. The second arched frame may define a second plurality of apertures. The dental device may further include a receiving mechanism coupled to the lingual portion of the second arched frame and a second moldable tray coupled to the second arched frame. The second moldable tray may engage the second plurality of apertures and may comprise a second channel configured to engage at least some of the teeth of the user's mandibular arch. The hook may engage the receiving mechanism and the threaded adjustor may adjust the forward position of the arched frame relative to the second arched frame.

In another embodiment, a universal oral appliance is provided comprising an arched frame. The arched frame may be configured to be positioned proximate to the occlusal surface of a user's dental arch such that the arched frame extends beyond the cuspids of the user's dental arch when the universal oral appliance is inserted in the user's mouth. The arched frame may have a midline that aligns substantially with the anterior midline of the user's mouth when the universal oral appliance is inserted in the user's mouth. The arched frame may define a plurality of apertures and may comprise a universal coupler configured to removably engage a dental attachment. The universal coupler may comprise a substantially planar surface proximate to and extending across the midline of the arched frame. The universal coupler may be configured to be positioned proximate to the occlusal surface of a user's incisors when the universal oral appliance is inserted in the user's mouth. The universal coupler may further comprise a first rail coupled to a first end of the substantially planar surface and a second rail coupled to a second end of the substantially planar surface. The first rail, second rail, and substantially planar surface may define a slot.

In another embodiment, a kit for use in constructing a universal oral appliance is provided. The kit may comprise an arched frame and a plurality of dental attachments. The arched frame may be configured to be positioned proximate to the occlusal surface of a user's dental arch such that the arched frame extends beyond the cuspids of the user's dental arch when the universal oral appliance is inserted in the user's mouth. The arched frame may have a midline that aligns substantially with the anterior midline of the user's mouth when the universal oral appliance is inserted in the user's mouth. The arched frame may define a plurality of apertures and may comprise a universal coupler. The universal coupler may comprise a substantially planar surface proximate to and extending across the midline of the arched frame. The substantially planar surface may be configured to be positioned proximate to the occlusal surface of a user's incisors when the universal oral appliance is inserted in the user's mouth. The universal coupler may further comprise a first rail coupled to a first end of the substantially planar surface and a second rail coupled to a second end of the substantially planar surface. The first rail, second rail, and substantially planar surface may define a slot. The kit may further comprise a plurality of dental attachments comprising a rounded projection configured to be the point of contact between the user's upper and lower dental arches to prevent the user from clenching his jaw. The plurality of dental attachments may further comprise a hook configured to engage a receiving mechanism such that the forward position of a second arched frame may be adjusted relative to the position of the arched frame.

In another embodiment, a universal oral appliance is provided comprising an arched frame, a moldable tray, and a plurality of dental attachments. The arched frame may be configured to be positioned proximate to the occlusal surface of a user's dental arch such that the arched frame extends beyond the cuspids of the user's dental arch when the universal oral appliance is inserted in the user's mouth. The arched frame may have a midline that aligns substantially with the anterior midline of the user's mouth when the universal oral appliance is inserted in the user's mouth. The arched frame may define a plurality of apertures and may comprise a universal coupler. The universal coupler may comprise a substantially planar surface proximate to and extending across the midline of the arched frame. The substantially planar surface may be configured to be positioned proximate to the occlusal surface of a user's incisors when the universal oral appliance is inserted in the user's mouth. The universal coupler may further comprise a first rail coupled to a first end of the substantially planar surface and a second rail coupled to a second end of the substantially planar surface. The first rail, second rail, and substantially planar surface may define a slot. The moldable tray may be coupled to the arched frame and may comprise a channel configured to engage at least some of the teeth of the user's dental arch. The dental attachment may include a substantially rounded projection configured to be the point of contact between the user's upper and lower dental arches to prevent the user from clenching his jaw. The dental attachment may be an adjustable hook configured to engage the receiving mechanism such that the forward position of the arched frame is adjustable relative to the position of a second arched frame. The dental attachment may be a handle.

In another embodiment, a dental device is provided comprising an arch, a dental attachment with an anchoring element, a second arch with a second anchoring element, and a tension element. The arch may be configured to engage at least some of the teeth of a user's dental arch and may have a midline that aligns substantially with the anterior midline of the user's mouth when the arch is inserted in the user's mouth. The dental attachment may be configured to engage the arch along the midline of the arch. The dental attachment may comprise an anchoring element configured to be outside the user's mouth when the arch is inserted in the user's mouth. The second arch may be configured to engage at least some of the teeth of a user's second dental arch. The second arch may have a midline that aligns substantially with the anterior midline of the user's mouth when the second arch is inserted in the user's mouth. The second anchoring element may be coupled to the second arch along the midline of the second arch. The tension element may be configured to engage the second anchoring element. The tension element may be further configured to couple to the anchoring element outside the user's mouth when the arch is inserted in the user's mouth.

In another embodiment, a kit for constructing a dental device is provided. The kit may comprise an arch, a dental attachment with an anchoring element, a second arch with a second anchoring element, and a tension element. The arch may be configured to engage at least some of the teeth of a user's dental arch and may have a midline that aligns substantially with the anterior midline of the user's mouth when the arch is inserted in the user's mouth. The dental attachment may be configured to engage the arch along the midline of the arch. The dental attachment may comprise an anchoring element configured to be outside the user's mouth when the arch is inserted in the user's mouth. The second arch may be configured to engage at least some of the teeth of a user's second dental arch. The second arch may have a midline that aligns substantially with the anterior midline of the user's mouth when the second arch is inserted in the user's mouth. The second anchoring element may be coupled to the second arch along the midline of the second arch. The tension element may be configured to engage the second anchoring element. The tension element may be further configured to couple to the anchoring element outside the user's mouth when the second arch is inserted in the user's mouth.

In another embodiment, a dental device is provided comprising an arched frame, a moldable tray, a dental attachment with an anchoring element, a second arched frame with a second anchoring element, a second moldable tray, and a tension element. The arched frame may be configured to be positioned proximate to the occlusal surface of a user's maxillary arch such that the arched frame extends beyond the cuspids of the user's maxillary arch. The arched frame may define a plurality of apertures. The moldable tray may be coupled to the arched frame and may engage the plurality of apertures. The moldable tray may comprise a channel configured to engage at least some of the teeth of the user's maxillary arch. The dental attachment may be configured to removably engage the arch along the midline of the arch. The dental attachment may comprise an anchoring element configured to be outside the user's mouth when the arch is inserted in the user's mouth. The second arched frame may be configured to be positioned proximate to the occlusal surface of a user's mandibular arch such that the second arched frame extends beyond the cuspids of the user's mandibular arch. The second arched frame may define a second plurality of apertures. The second moldable tray may be coupled to the second arched frame and may engage the second plurality of apertures. The second moldable tray may comprise a channel configured to engage at least some of the teeth of the user's mandibular arch. The second anchoring element may be coupled to the second arch along the midline of the second arch. The tension element may be configured to removably engage the second anchoring element. The tension element may be configured to couple to the anchoring element outside the user's mouth when the second arch is inserted in the user's mouth. The dental attachment may comprise a post and a buckle coupled to a first end of the post. A second end of the post may engage the arch. The tension element may comprise a coupler and a strap coupled to the coupler. The coupler may engage the second anchoring element. A length of the strap may be configured to engage the buckle. The buckle may be configured to substantially secure the length of the strap engaging it. By increasing the length of the strap engaging the buckle, the forward position of the arched frame relative to the second arched frame may be adjusted.

Previous dental devices may be constructed in labs independent of a dentist's office. Labs could not construct custom dental devices for particular patients without first having the patients' dental impressions. Labs may also charge patients an extra fee for constructing the dental devices. In particular embodiments, the dental device may be constructed at the dentist's office without sending dental impressions to a lab, thus saving patients time and money. Furthermore, previous dental devices may be created to treat only one disorder (such as, for example, snoring or jaw-clenching). In particular embodiments, the dental device may be customized to treat multiple dental problems. As an example, and not by way of limitation, the dental device may comprise a universal coupler configured to engage various dental attachments. Each dental attachment may be designed to treat a different disorder. Additionally, previous dental devices may limit the lower jaw's range of motion when the dental devices were inserted in the user's mouth. Previous dental devices may also limit a third party's access to the user's mouth when the dental device is in the user's mouth. In particular embodiments, the dental device may comprise a tension element engaging an anchoring element outside the user's mouth. The tension element and anchoring element may pull the user's lower jaw forward without locking the user's lower jaw in place. Furthermore, a third party may pull on the tension element to open the user's airway, or a third party may release the tension element from the anchoring element to quickly gain access to a user's mouth. Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

FIG. 3A illustrates an example arched frame comprising an adjustment mechanism, and an example moldable tray.
FIG. 3B illustrates an example arched frame comprising a receiving mechanism, and an example moldable tray.
FIG. 3C illustrates an example arched frame comprising an adjustment mechanism, and an example moldable tray.
FIG. 3D illustrates an example arched frame comprising a receiving mechanism, and an example moldable tray.

DETAILED DESCRIPTION OF THE INVENTION

Figure 1:
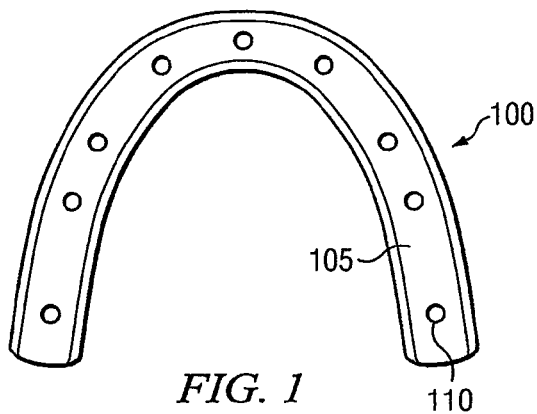
FIG. 1 illustrates an example arched frame.
Figure 2A:
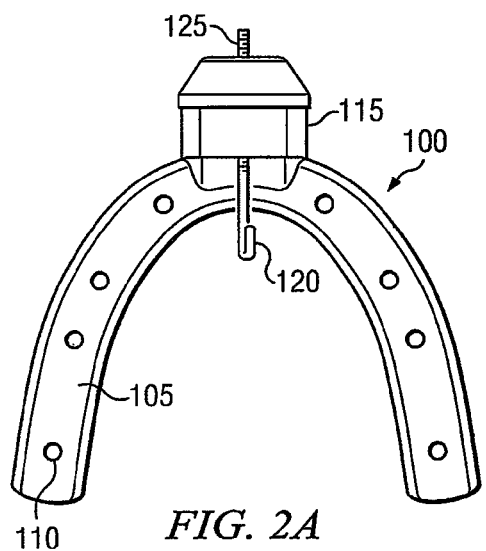
FIG. 2A illustrates an example arched frame comprising an adjustment mechanism.
Figure 2B:
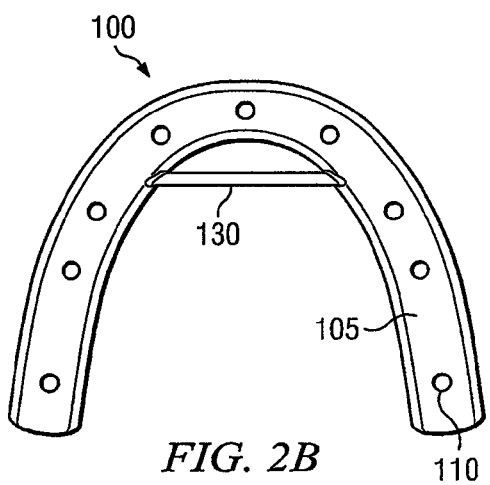
FIG. 2B illustrates an example arched frame comprising a receiving mechanism.
Figure 2C:
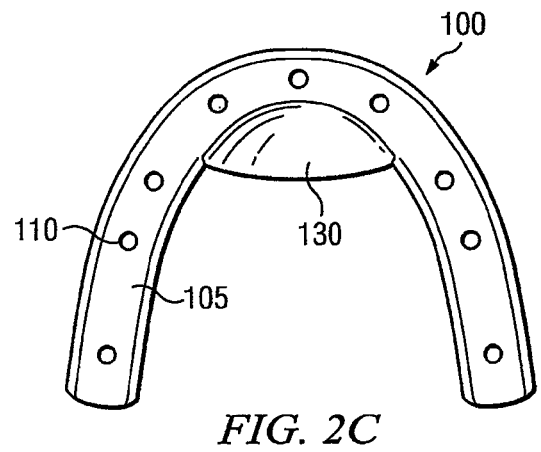
FIG. 2C illustrates an example arched frame comprising a receiving mechanism.

FIG. 1 illustrates an example arched frame 100. Arched frame 100 may comprise an arched body 105 that defines a plurality of apertures 110 through arched frame 100. In particular embodiments, arched frame 100 may be configured to be positioned proximate to the occlusal surface of a user's dental arch. In some embodiments, arched frame 100 may extend beyond the cuspids of the user's dental arch when arched frame 100 is inserted in the user's mouth. In some embodiments, arched frame 100 may have a consistent thickness between 1.5 and 2 millimeters. FIG. 2A illustrates an example arched frame comprising an adjustment mechanism. As shown in FIG. 2A, an arched frame 100 is provided comprising an arched body 105 defining a plurality of apertures 110 and an adjustment mechanism 115. In particular embodiments, arched body 105 may define a plurality of grooves, or a slot. Adjustment mechanism 115 may be coupled to arched body 105 along the midline of arched frame 100. In certain embodiments, Adjustment mechanism 115 may comprise a hook 120 and a threaded adjustor 125. FIGS. 2B and 2C illustrate arched frames each comprising a receiving mechanism. As shown in FIGS. 2B and 2C, an arched frame 100 is provided comprising an arched body 105 defining a plurality of apertures 110 and a receiving mechanism 130. In particular embodiments, receiving mechanism 130 may be a bar spanning a portion of the arch of arched body 105. In other embodiments, receiving mechanism 130 may be a surface coupled to the lingual portion of arched frame 100. In some embodiments, the surface may be rounded.

In particular embodiments, arched frame 100 may be formed from any material suitable for dental uses, for example, a hard plastic. Arched frame 100 may be formed from methyl methacrylate or a polycarbonate resin thermoplastic such as that sold under the Registered Trademark Lexan. Such materials are known to those familiar with dental devices, and other suitable materials may be used to form arched frame 100 without departing from the intended scope of the present invention.

FIGS. 3A and 3C illustrate example arched frames each comprising an adjustment mechanism and example moldable trays. As shown in FIGS. 3A and 3C, an arched frame 100 and a moldable tray 135 are provided. Arched frame 100 may comprise an arched body 105 defining a plurality of apertures 110 and an adjustment mechanism 115. Moldable tray 135 may be coupled to arched frame 100 and may engage the plurality of apertures 110. In particular embodiments, moldable tray 135 may form through plurality of apertures 110 to couple to two sides of arched body 105. In some embodiments, moldable tray 135 may form into a plurality of grooves defined by arched body 105. In some embodiments, moldable tray 135 may be secured to arched frame 100 by forming through a slot defined by arched body 105. Moldable tray 135 may further comprise a channel 140 that is configured to engage at least some of a user's dental arch. In particular embodiments, channel 140 may engage the incisors and cuspids of the user's dental arch. In some embodiments, channel 140 may engage the incisors, cuspids, and some of the molars of the user's dental arch. In some embodiments, channel 140 may engage the incisors, cuspids, and all the molars of the user's dental arch. In particular embodiments, channel 140 may be shaped to conform to a generic user's teeth. In other embodiments, channel 140 may be a smooth channel that covers a user's teeth. In particular embodiments, channel 140 may be further shaped to conform to a particular user's teeth.

In particular embodiments, moldable tray 135 may comprise a polycaprolactone polymer or other aliphatic polyester. One or more of the polycaprolactone polymers may have the formula:

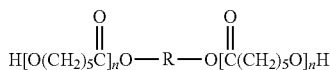

where R is an aliphatic hydrocarbon and n may range from approximately 300 to approximately 650. The present invention contemplates polycaprolactone polymers using other suitable formulas.

Moldable tray 135 may include any suitable polycaprolactone polymer or other aliphatic polyester, for example, and not by way of limitation, the TONE P 700, TONE P 767, or TONE P 787 polycaprolactone polymers manufactured by Union Carbide Corporation, taken singly or in any combination. A suitable light cured material, another polymer, or any other suitable material, such as a filler, coloring agent, stabilizer, antioxidant, or antimicrobial agent, may be used to replace or combine with one or more of the polycaprolactone polymers in forming a deformable material 20 having any number of characteristics, properties, or uses.

The TONE polycaprolactone polymers are described in U.S. Pat. Nos. 5,112,225 and 4,784,123, and in literature distributed by Union Carbide Corporation, as homopolymers, block copolymers, graft copolymers, or other polymers that contain epsilon caprolactone. Polymerization may be initiated using one or more diols, for example, and not by way of limitation, ethylene glycol; diethylene glycol; neopentyl glycol; butane diol; hexane diol; or any other suitable diol.

In particular embodiments, moldable tray 135 may be custom molded to a user's teeth. For example, moldable tray 135 may comprise a material that is moldable when heated. Once heated, the material may be pressed around a user's dental arch to form a moldable tray 135 that conforms to the user's teeth. In particular embodiments, moldable tray 135 may be used with arched frame 100 to form a custom dental device. For example, arched frame 100 may comprise a hard plastic material. When moldable tray 135 is forming around a user's teeth, arched frame 100 may be pressed against moldable tray 135, so that mold tray 135 forms through plurality of apertures 110 defined by arched body 105. As moldable tray 135 cools and hardens, moldable tray 135 may couple to arched frame 100 through plurality of apertures 110. In some embodiments, moldable tray 135 may couple to arched frame 100 through a slot or by forming into a plurality of grooves. In particular embodiments, arched frame 100 may provide structural support for moldable tray 135 as moldable tray 135 engages the user's teeth. For example, as moldable tray 135 engages the user's teeth, arched frame 100 may prevent moldable tray 135 from deforming or shifting under the stresses caused by movement of the user's mouth.

In particular embodiments, a custom dental device may comprise arched frame 100 and moldable tray 135. A dentist may be able to construct the custom dental device for a patient without having to send the patient's dental impressions to a lab. The dentist may heat moldable tray 135 and press moldable tray 135 around the user's teeth. The dentist may then press arched frame 100 against moldable tray 135 to construct the custom dental device. As a result, the patient may not have to wait for the lab to create the dental device, nor does the patient have to pay an extra fee charged by the lab.

FIG. 3B and 3D illustrate example arched frames each comprising a receiving mechanism, and example moldable trays. As shown in FIGS. 3B and 3D, an arched frame 100 and a moldable tray 135 are provided. Arched frame 100 may comprise an arched body 105 defining a plurality of apertures 110 and a receiving mechanism 130. Receiving mechanism 130 may be coupled to arched body 105. In particular embodiments, receiving mechanism 130 may be a bar that spans a portion of the arch of arched body 105. Moldable tray 135 may comprise a channel 140 that is configured to engage at least some of the teeth of a user's dental arch.

Figure 4:
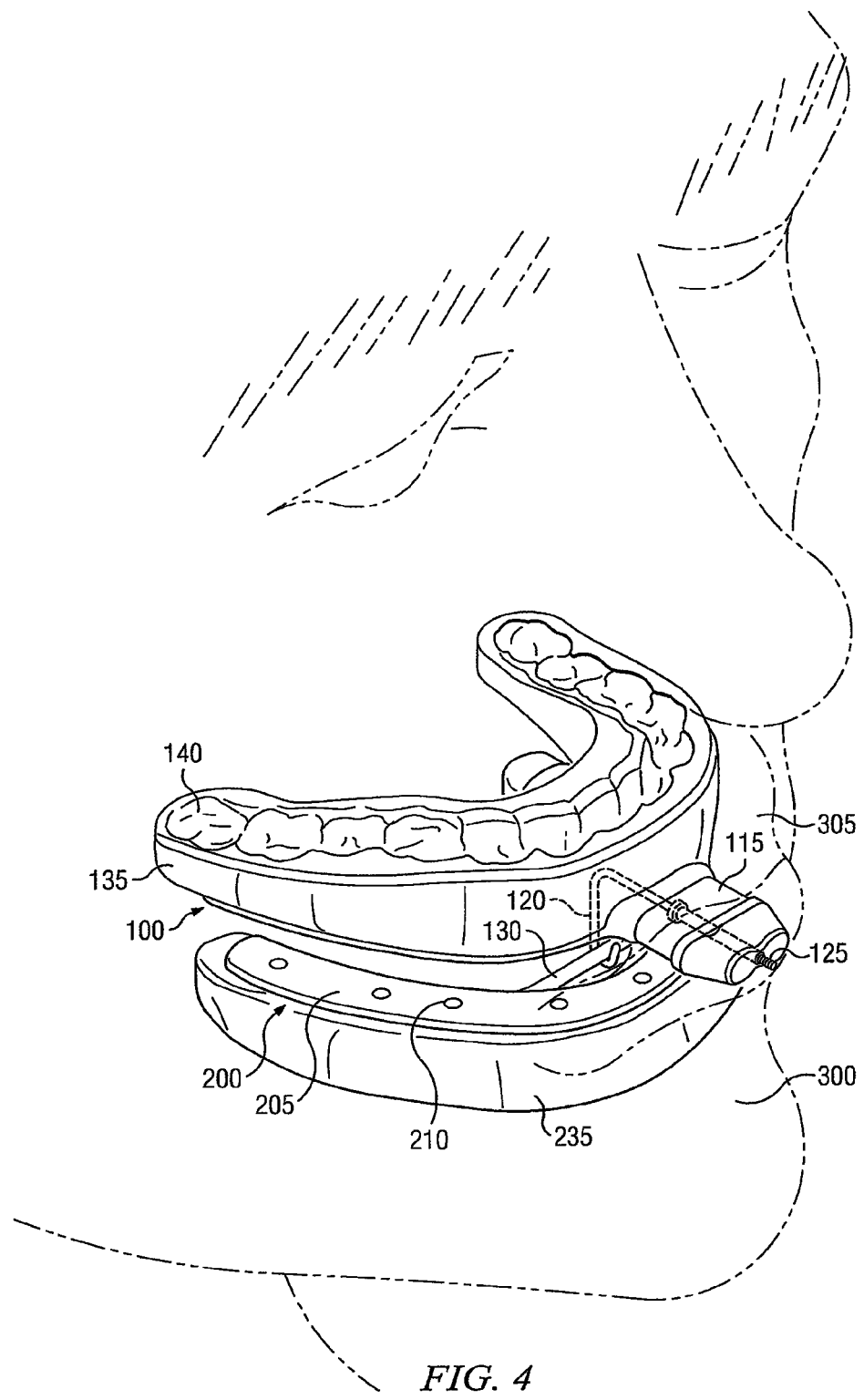
FIG. 4 illustrates an example dental device in a user's mouth.

FIG. 4 illustrates an example dental device in a user's mouth. As shown in FIG. 4, a dental device is provided that comprises an arched frame 100, a moldable tray 135, a second arched frame 200, and a second moldable tray 235. Arched frame 100 may comprise an adjustment mechanism 115 that comprises a hook 120 and a threaded adjustor 125. Moldable tray 135 may be coupled to arched frame 100. Moldable tray 100 may comprise a channel 140. In some embodiments, channel 140 may be shaped to conform to a generic user's maxillary arch 305. In other embodiments, channel 140 may be a smooth channel that covers some of teeth of a user's maxillary arch 305. In particular embodiments, channel 140 may be further shaped to conform to a particular user's maxillary arch 305. Second arched frame 200 may comprise a second arched body 205 defining a second plurality of apertures 210. Second arched frame 200 may further comprise a receiving mechanism 130 coupled to the lingual portion of second arched body 205. In some embodiments, receiving mechanism 130 may be a bar that spans a portion of the arch of second arched body 205. Second moldable tray 235 may be coupled to second arched frame 200 and may engage second plurality of apertures 210. Second moldable tray 235 may be configured to engage some of the teeth of the user's mandibular arch 300. In particular embodiments, hook 120 may engage receiving mechanism 130. Threaded adjustor 125 may be used to adjust the forward position of arched frame 100 relative to second arched frame 200. The relative positions of the two arched frames 100 and 200 may adjust the position of the user's maxillary arch 305 relative to the user's mandibular arch 300. In some embodiments, the relative position of the user's maxillary and mandibular arches may help to improve a user's breathing and/or prevent the user from snoring while sleeping.

Figure 5A:
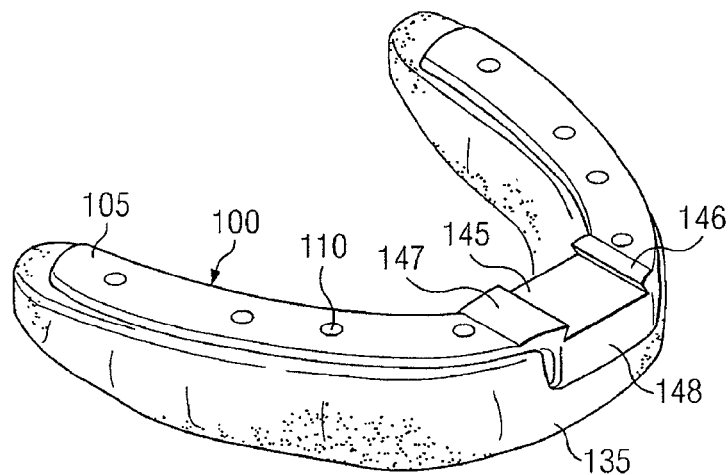
FIG. 5A illustrates an example universal oral appliance comprising a universal coupler.
Figure 5B:
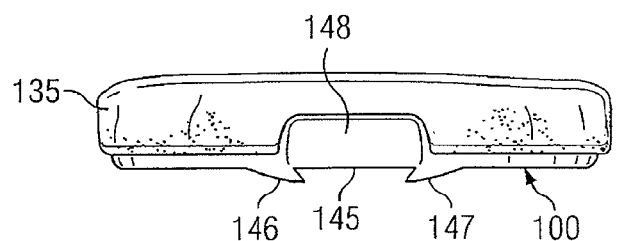
FIG. 5B illustrates an example universal oral appliance comprising a universal coupler.

FIGS. 5A and 5B each illustrate an example universal oral appliance comprising a universal coupler. As shown in FIG. 5A and 5B, a universal oral appliance is provided comprising an arched frame 100 and a moldable tray 135 coupled to arched frame 100. Arched frame 100 may comprise an arched body 105 defining a plurality of apertures 110. In particular embodiments, arched frame 100 may be configured to be positioned proximate to the occlusal surface of a user's dental arch such that arched frame 100 extends beyond the cuspids of the user's dental arch when arched frame 100 is inserted in the user's mouth. Arched frame 100 may have a midline that aligns substantially with the anterior midline of the user's mouth when arched frame 100 is inserted in the user's mouth. Arched frame 100 may further comprise a universal coupler. In particular embodiments, the universal coupler may comprise a substantially planar surface 145, a first rail 146, and a second rail 147. Substantially planar surface 145 may be proximate to and extend across the midline of arched frame 100. In particular embodiments, substantially planar surface 145 may be configured to be positioned proximate to the occlusal surface of a user's incisors when the universal oral appliance is inserted in the user's mouth. First rail 146 may be coupled to a first end of substantially planar surface 145. In particular embodiments, first rail 146 may be distal to the midline of arched frame 100. In other embodiments, first rail 146 may be anterior to arched frame 100. Second rail 147 may be coupled to a second end of substantially planar surface 145. In particular embodiments, second rail 147 may be distal to the midline of arched frame 100. In other embodiments, second rail 147 may be posterior to arched frame 100. First rail 146 and second rail 147 may form an acute angle with substantially planar surface 145. In particular embodiments, first rail 146, second rail 147, and substantially planar surface 145 may define a slot. In particular embodiments, a dental attachment may slide into the slot and engage arched frame 100. In some embodiments, the universal coupler may comprise a locking mechanism (such as, for example, a screw, a tab, or a groove). The screw may secure a dental attachment to the universal coupler by screwing through the dental attachment and into the universal coupler. The tab may secure the dental attachment by engaging the exterior of the dental attachment or by engaging a slot in the dental attachment. The groove may secure the dental attachment by frictionally engaging the dental attachment. In particular embodiments, the universal coupler may further comprise a stop 148 coupled to substantially planar surface 145. Stop 148 may be coupled to the labial or lingual ends of substantially planar surface 145. Alternatively, stop 148 may be coupled to a distal end of substantially planar surface 145. Although this disclosure describes a universal oral appliance comprising arched frame 100, moldable tray 135, and a universal coupler coupled to arched frame 100, this disclosure contemplates a one-piece piece universal oral appliance and a universal coupler coupled to the universal oral appliance.

Figure 5C:
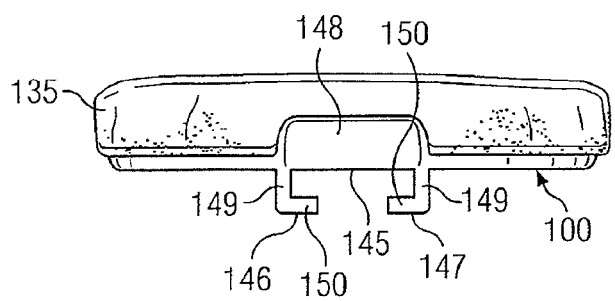
FIG. 5C illustrates an example universal oral appliance comprising a universal coupler.

FIG. 5C illustrates an example universal oral appliance comprising a universal coupler. As shown in FIG. 5C, a universal oral appliance is provided comprising an arched frame 100 and a moldable tray 135 coupled to arched frame 100. Arched frame 100 may comprise a universal coupler comprising a substantially planar surface 145, a first rail 146, a second rail 147, and a stop 148. In particular embodiments, each rail 146 and 147 may comprise a first segment 149 and a second segment 150. First segment 149 may be coupled at a first end to substantially planar surface 145, and second segment 150 may be coupled to a second end of first segment 149. In particular embodiments, first segment 149 and second segment 150 may be substantially perpendicular to each other.

Figure 5D:
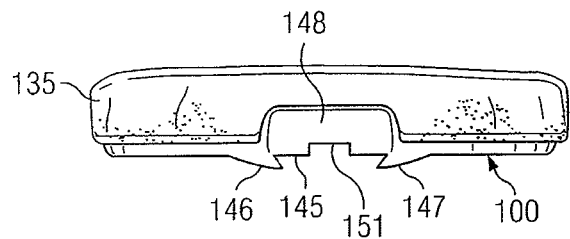
FIG. 5D illustrates an example universal oral appliance comprising a universal coupler comprising a guided channel.

FIG. 5D illustrates an example universal oral appliance comprising a universal coupler comprising a guided channel. As shown in FIG. 5D, a universal oral appliance is provided comprising an arched frame 100 and a moldable tray 135. Arched frame 100 may comprise a universal coupler comprising a substantially planar surface 145, a first rail 146, a second rail 147, and a stop 148. First rail 146, second rail 147, and substantially planar surface 145 may define a slot. In particular embodiments, the universal coupler may further comprise a guided channel 151. Guided channel 151 may be configured to guide a dental attachment through the slot.

Figure 5E:
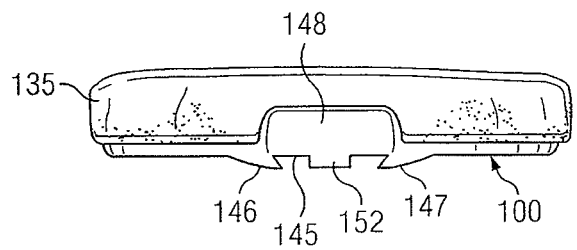
FIG. 5E illustrates an example universal oral appliance comprising a universal coupler comprising a raised surface.

FIG. 5E illustrates an example universal oral appliance comprising a universal coupler comprising a raised surface 152. As shown in FIG. 5E, a universal oral appliance is provided comprising an arched frame 100 and a moldable tray 135. Arched frame 100 may comprise a universal coupler comprising a substantially planar surface 145, a first rail 146, a second rail 147, and a stop 148. First rail 146, second rail 147, and substantially planar surface 145 may define a slot. In particular embodiments, the universal coupler may further comprise a raised surface 152. Raised surface 152 may be configured to guide a dental attachment through the slot. In particular embodiments, raised surface 152 may be further configured to secure or lock the dental attachment.

Figure 6:
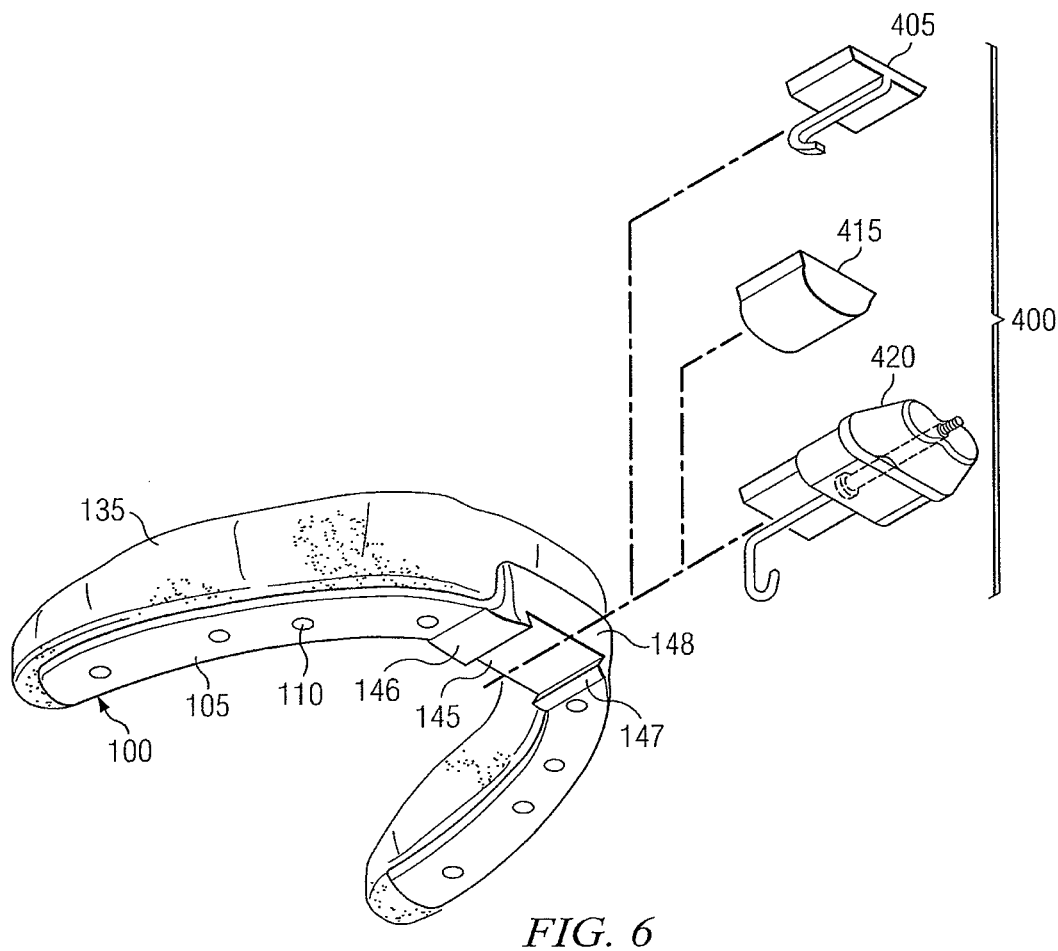
FIG. 6 illustrates an example universal oral appliance comprising a universal coupler, and an example plurality of dental attachments.

FIG. 6 illustrates an example universal oral appliance comprising a universal coupler, and an example plurality of dental attachments 400. As shown in FIG. 6, an example universal oral appliance is provided that comprises an arched frame 100 and a moldable tray 135. Arched frame 100 comprises an arched body 105 that defines a plurality of apertures 110. Arched frame 100 further comprises a universal coupler. The universal coupler may comprise a substantially planar surface 145, a first rail 146, a second rail 147, and a stop 148. In particular embodiments, first rail 146, second rail 147, and substantially planar surface 145 may define a slot. FIG. 6 also illustrates a plurality of dental attachments 400. In particular embodiments, the plurality of dental attachments 400 may comprise dental attachments configured to treat different disorders. For example, the plurality of dental attachments 400 may include a hook 405, a substantially rounded projection 415, and an adjustable hook 420. Other attachments may include a handle or any other appropriate attachment configured for use with an oral appliance. A user or a medical professional may choose which dental attachment to use without having to hire a lab to construct a new oral appliance. In some embodiments, dental attachments 400 may be configured to engage the slot.

Figure 7:
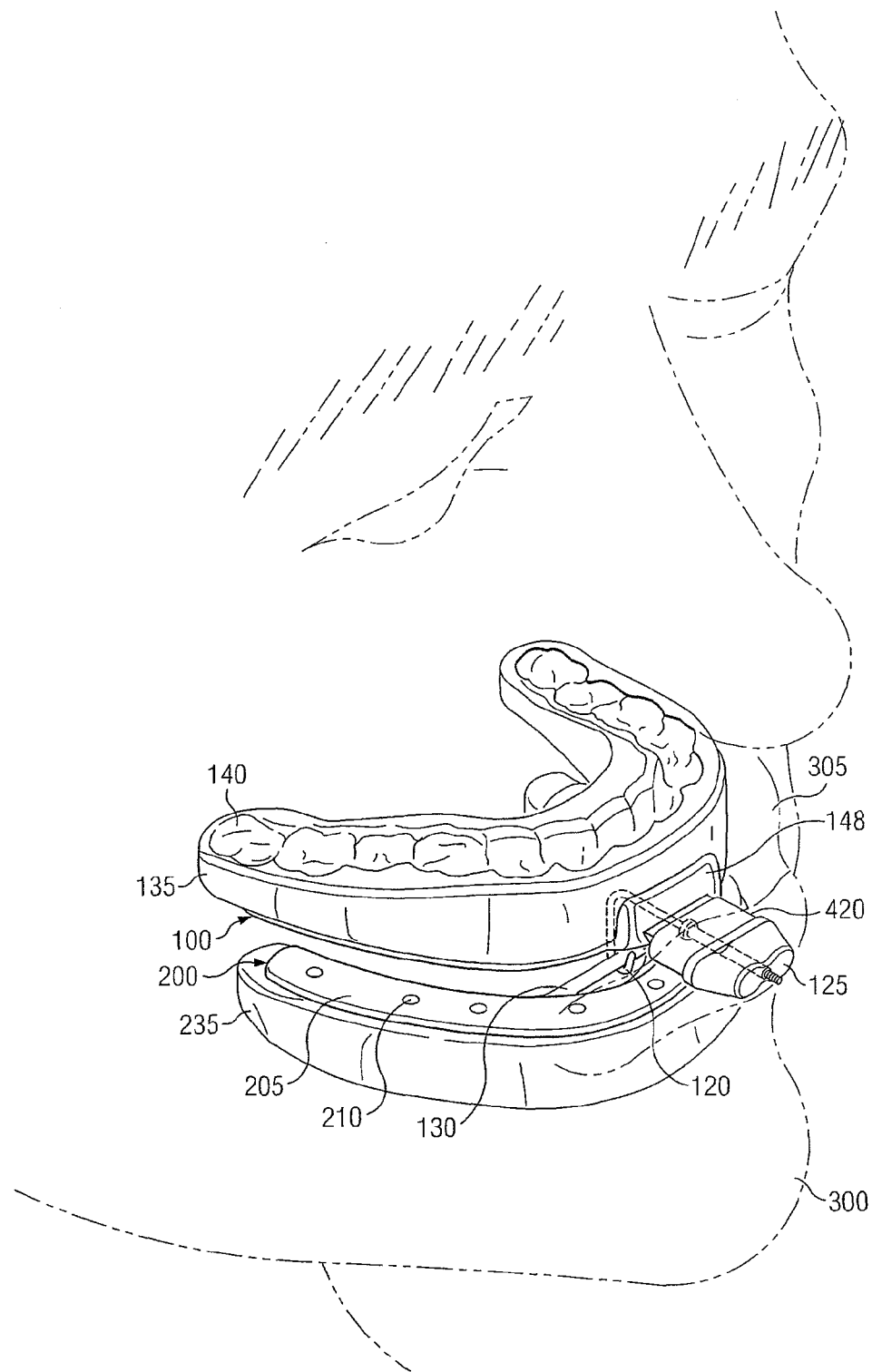
FIG. 7 illustrates an example dental device in a user's mouth.

FIG. 7 illustrates an example dental device in a user's mouth. As shown in FIG. 7, a dental device is provided that comprises an arched frame 100, a moldable tray 135 coupled to arched frame 100, a second arched frame 200, and a second moldable tray 235 coupled to arched frame 200. Arched frame 100 may comprise a universal coupler. The universal coupler may comprise a stop 148. Moldable tray 135 may comprise a channel 140 that is configured to engage at least some of the teeth of the user's maxillary arch 305. Second arched frame 200 may comprise a second arched body 205 that defines a second plurality of apertures 210. Second arched frame 200 may further comprise a receiving mechanism 130 that spans the lingual portion of second arched frame 200. In particular embodiments, receiving mechanism 130 may be a bar. Second moldable tray 235 may engage second plurality of apertures 210. The dental device further comprises a dental attachment that is configured to engage the universal coupler. In some embodiments, the dental attachment may be an adjustable hook 420 that comprises a hook 120 and a threaded adjustor 125. Hook 120 may engage receiving mechanism 130. Threaded adjustor 125 may be used to adjust the forward position of second arched frame 200 relative to arched frame 100. This adjustment may adjust the forward position of the user's mandibular arch 300 relative to the position of the user's maxillary arch 305. In some embodiments, this adjustment may help to prevent the user from snoring while sleeping.

Figure 8:
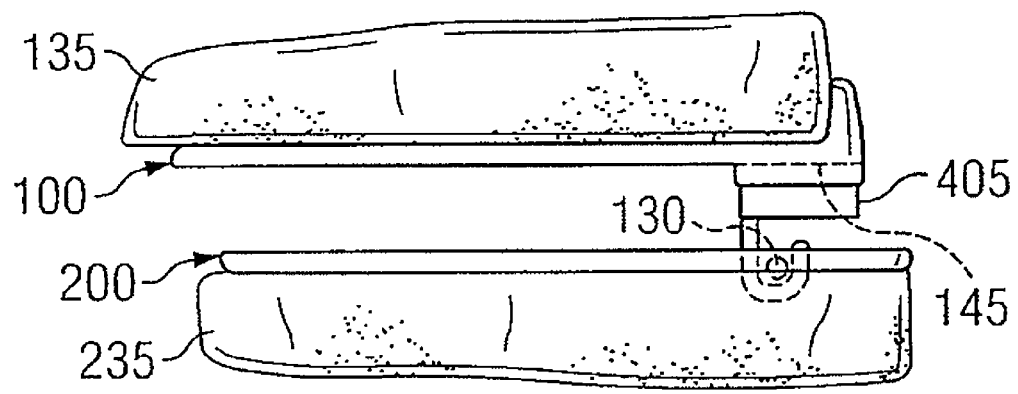
FIG. 8 illustrates an example dental device comprising a universal coupler and an example dental attachment.

FIG. 8 illustrates an example dental device comprising a universal coupler and an example dental attachment. As shown in FIG. 8, a dental device is provided comprising an arched frame 100, a moldable tray 135, a second arched frame 200, and a second moldable tray 235. Arched frame 100 may comprise a universal coupler comprising a substantially planar surface 145. In particular embodiments, a hook 405 may be configured to engage the universal coupler. In particular embodiments, second arched frame 200 may comprise a receiving mechanism 130 coupled to the lingual portion of second arched frame 200. Receiving mechanism 130 may be a bar that spans the lingual portion of second arched frame 200. In particular embodiments, hook 405 may engage receiving mechanism 130 to adjust the forward position of arched frame 100 relative to second arched frame 200. In certain embodiments, this adjustment may help to prevent a user from snoring when the dental device is inserted in the user's mouth.

Figure 9:
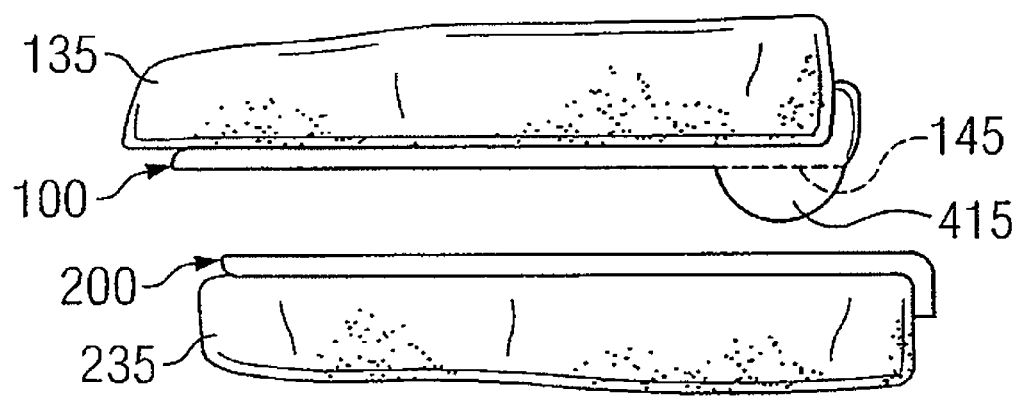
FIG. 9 illustrates an example dental device comprising a universal coupler and an example dental attachment.

FIG. 9 illustrates an example dental device comprising a universal coupler and an example dental attachment. As shown in FIG. 9, a dental device is provided comprising an arched frame 100, a moldable tray 135, a second arched frame 200, and a second moldable tray 235. Arched frame 100 may comprise a universal coupler comprising a substantially planar surface 145. In particular embodiments, a substantially rounded projection 415 may be configured to engage the universal coupler. In particular embodiments, rounded projection 415 may be the only point of contact between the user's upper and lower dental arches to prevent a user from clenching his jaw when the dental device is inserted in the user's mouth. In particular embodiments, rounded projection 415 may contact an opposing arch or may contact one or more incisors of the opposing dental arch to prevent a user from clenching his jaw when the dental device is inserted in the user's mouth. The opposing arch may have a contact surface that may be planar.

The universal oral appliance comprising a universal coupler may provide several advantages for a user. In particular embodiments, a universal oral appliance comprising a universal coupler may offer more use options to a user. For example, a user's appliance may be fitted with several different dental attachment options. The user may choose which dental attachment is best suited for his situation without having to hire a lab to construct another appliance. In particular embodiments, a particular user may also adjust the dental attachment to better suit the shape and size of the user's mouth. This disclosure contemplates the universal oral appliance being created from parts in a kit. A user may purchase the kit instead of a dental device created in a laboratory.

Figure 10:
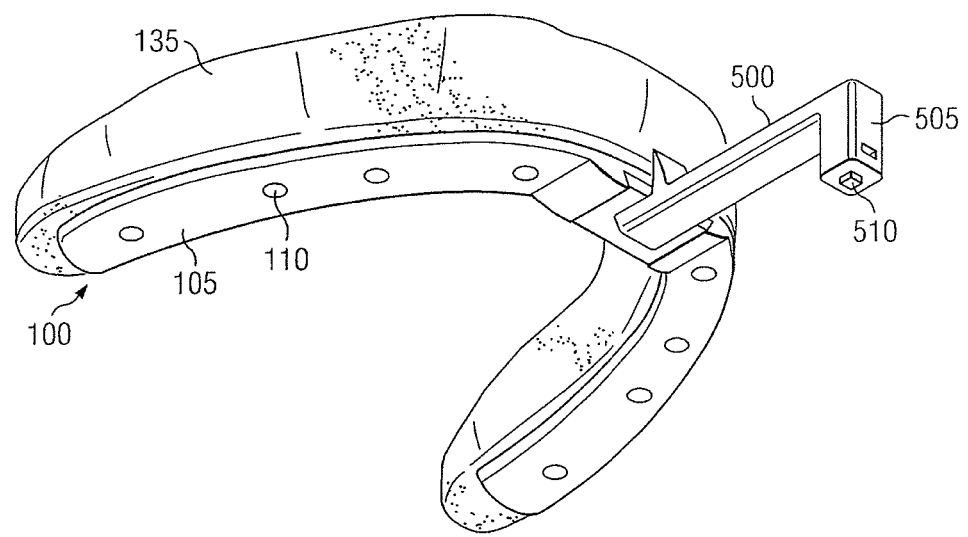
FIG. 10 illustrates an example arch comprising a dental attachment.

FIG. 10 illustrates an example arch comprising a dental attachment. As shown in FIG. 10, an arch is provided that comprises an arched frame 100 and a moldable tray 135 coupled to arched frame 100. Arched frame 100 comprises an arched body 105 that defines a plurality of apertures 110. The arch may further comprise a dental attachment configured to engage arched frame 100. In particular embodiments, the dental attachment is configured to engage arched frame 100 along the midline of arched frame 100. In particular embodiments, the dental attachment may comprise a post 500 and an anchoring element 505. Post 500 may be coupled at a first end to anchoring element 505. In particular embodiments, a second end of post 500 may engage arched frame 100. In some embodiments, post 500 may be configured to removably engage arched frame 100. In particular embodiments, anchoring element 505 may include a buckle, a slot, a clasp, a clamp, and/or any other appropriate element to anchor a tension element. In some embodiments, anchoring element 505 may be configured to be outside a user's mouth when the arch is inserted in the user's mouth. In some embodiments, the dental attachment may further comprise a release mechanism 510. As an example and not by way of limitation, release mechanism 510 may be a button or a latch. Although this disclosure describes certain types of release mechanisms 510, this disclosure contemplates any suitable release mechanism 510. Although this disclosure describes an arch comprising arched frame 100, moldable tray 135, and a dental attachment, this disclosure contemplates a one-piece arch comprising a dental attachment.

Figure 11:
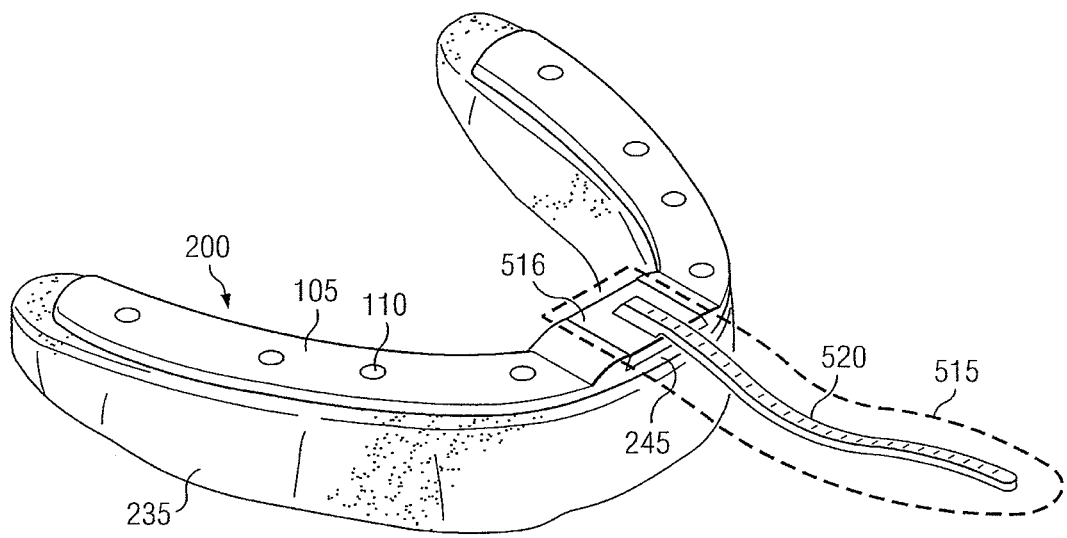
FIG. 11 illustrates an example arch comprising a tension element.

FIG. 11 illustrates an example arch comprising a second anchoring element and a tension element. As shown in FIG. 11, an arch is provided that comprises an arched frame 200 and a moldable tray 235 coupled to arched frame 200. Arched frame 200 comprises an arched body 205 that defines a plurality of apertures 210. The arch may further comprise a second anchoring element 245. In particular embodiments, second anchoring element 245 may be coupled to the arch along the midline of the arch. The arch may further comprise a tension element 515. In particular embodiments, tension element 515 may be flexible and may be configured to engage second anchoring element 245. In particular embodiments, tension element 515 may be further configured to couple to an anchoring element outside a user's mouth when the arch is inserted in the user's mouth. In some embodiments, tension element 515 may comprise a strap 520 and a coupler 516. Coupler 516 may be configured to engage the second anchoring element. In particular embodiments, coupler 516 may be configured to removably engage the second anchoring element. Strap 520 may be coupled to coupler 516. In particular embodiments, strap 520 may be configured to engage the anchoring element outside the user's mouth when the arch is inserted in the user's mouth. In particular embodiments, strap 520 may comprise a hard plastic, leather, or metal. In certain embodiments, strap 520 may be a zip tie. In other embodiments, strap 520 may be a wire, belt, string, or any other appropriate element to engage the anchoring element. Although this disclosure describes an arch comprising arched frame 200, moldable tray 235, and tension element 515, this disclosure contemplates a one-piece arch comprising tension element 515.

Figure 12:
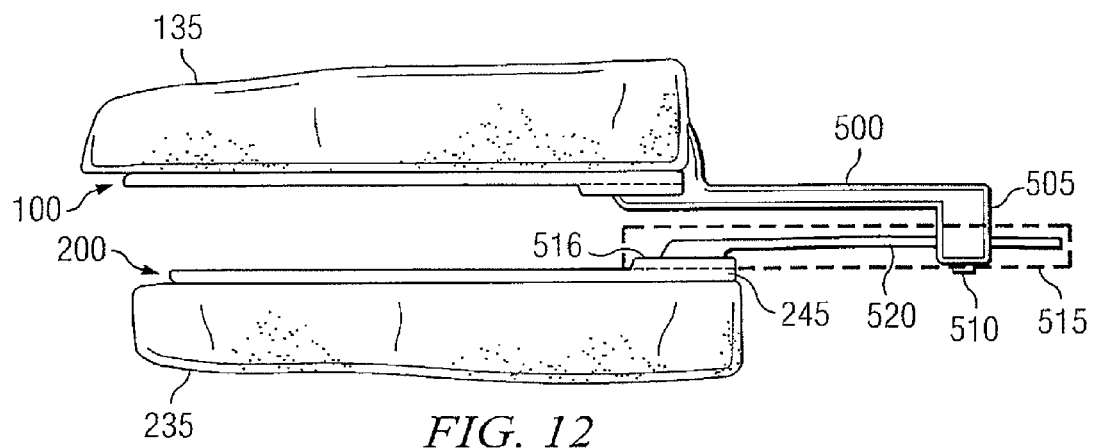
FIG. 12 illustrates an example dental device comprising a dental attachment and a tension element.

FIG. 12 illustrates an example dental device comprising a dental attachment, a second anchoring element, and a tension element. As shown in FIG. 12, a dental device is provided that comprises an arched frame 100 and a second arched frame 200. The dental device further comprises a moldable tray 135 coupled to arched frame 100 and a second moldable tray 235 coupled to second arched frame 200. The dental device may further comprise a dental attachment configured to engage arched frame 100. In particular embodiments, the dental attachment may comprise a post 500 and an anchoring element 505. The dental device may further comprise a second anchoring element 245. Second anchoring element 245 may be coupled to second arched frame 200. The dental device may further comprise a tension element 515. Tension element 515 may be configured to engage second anchoring element 245. In particular embodiments, tension element 515 may comprise a coupler 516 and a strap 520. In particular embodiments, strap 520 may be configured to engage anchoring element 505 outside the user's mouth when the dental device is inserted in the user's mouth. Anchoring element 505 may be configured to secure substantially the length of strap 520 engaged to anchoring element 505. In particular embodiments, increasing the length of strap 520 engaged to anchoring element 505 will adjust the forward position of arched frame 100 relative to second arched frame 200. In particular embodiments, the dental attachment may further comprise a release mechanism 510.

Figure 13:
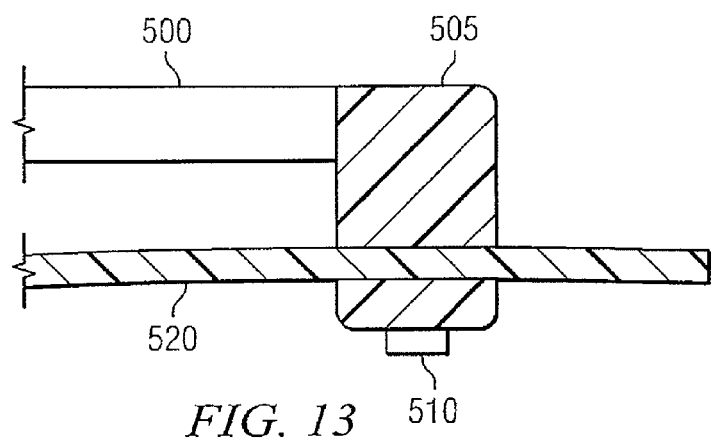
FIG. 13 illustrates an example dental attachment and tension element.

FIG. 13 illustrates an example dental attachment and tension element. As shown in FIG. 13, a dental attachment is provided comprising a post 500 and an anchoring element 505. Anchoring element 505 may be coupled to an end of post 500. A tension element is also provided comprising a strap 520. Strap 520 may be configured to engage anchoring element 505. Anchoring element 505 may be configured to secure the length of strap 520 engaged to anchoring element 505. In particular embodiments, the dental attachment may comprise a release mechanism 510. Release mechanism 510 may be configured to release strap 520 from anchoring element 505.

Figure 14:
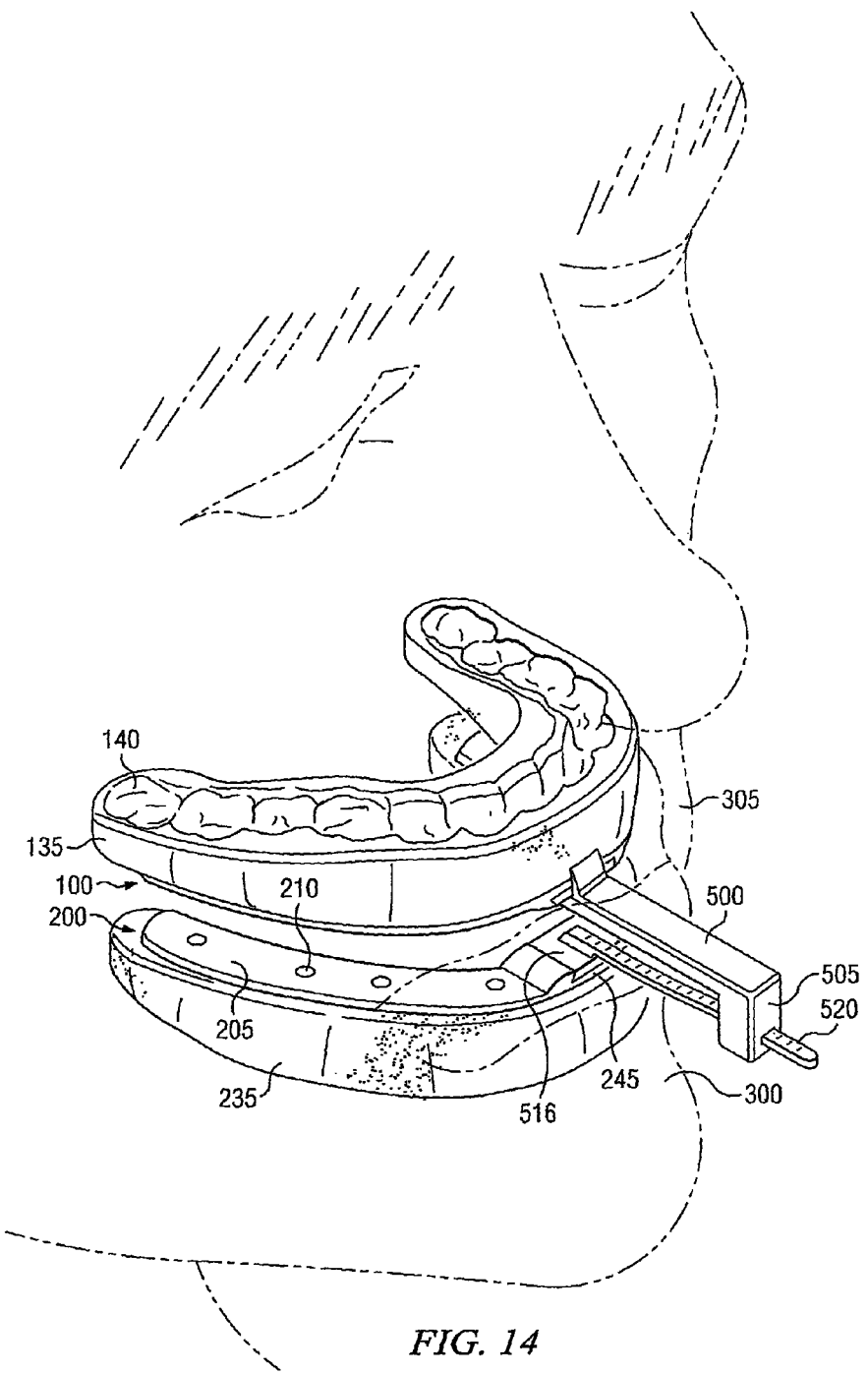
FIG. 14 illustrates an example dental device in a user's mouth.

FIG. 14 illustrates an example dental device in a user's mouth. As shown in FIG. 14, a dental device is provided that comprises an arched frame 100, a second arched frame 200, a moldable tray 135 coupled to arched frame 100, and a second moldable tray 235 coupled to second arched frame 200. Moldable tray 135 may comprise a channel 140 configured to engage at least some of the teeth of the user's maxillary arch 305. Second arched frame may comprise a second arched body 205 that defines a second plurality of apertures 210. The dental device may further comprise a dental attachment. The dental attachment may comprise a post 500 and an anchoring element 505. Anchoring element 505 may be coupled to an end of post 500, and a second end of post 500 may be configured to engage arched frame 100. Anchoring element 505 may be configured to be outside the user's mouth when the dental device is inserted in the user's mouth. The dental device may further comprise a second anchoring element 245 coupled to second arched frame 200. The dental device may further comprise a tension element comprising a coupler 516 and a strap 520. Coupler 516 may be configured to engage second anchoring element 245. Strap 520 may be coupled to coupler 516 and may be configured to engage anchoring element 520 outside the user's mouth when the dental device is inserted in the user's mouth. Anchoring element 505 may be configured to secure substantially the length of strap 520 engaged to anchoring element 505. In particular embodiments, increasing the length of strap 520 engaged to anchoring element 505 may adjust the forward position of arched frame 100 relative to second arched frame 200. In particular embodiments, adjusting the forward position of arched frame 100 relative to second arched frame 200 may adjust the forward position of the user's maxillary arch 305 relative to the user's mandibular arch 300. In particular embodiments, adjusting the forward position of the user's maxillary arch 305 relative to the position of the user's mandibular arch 300 may help to improve the user's breathing and/or prevent the user from snoring.

In particular embodiments, the dental device comprising a dental attachment and a tension element may allow a third party faster access to a user's mouth and airway. For example, if the user is a patient sleeping in a sleep laboratory, a doctor in the laboratory may quickly pull on the tension element to open an airway that closed while the patient slept. As another example, if the user is a patient undergoing surgery in a hospital, a surgeon may quickly release the tension element to open the patient's mouth for intubation or for insertion of an instrument while the patient is sedated. In particular embodiments, the dental device comprising a dental attachment and a tension element may pull the user's lower jaw forward without locking the lower jaw in place. The user's lower jaw will maintain a certain range of lateral motion while the dental device is inserted in the user's mouth. This disclosure contemplates the dental device comprising a dental attachment and a tension element being created from a kit. A patient, doctor, or surgeon may purchase the kit and create the dental device quickly. In particular embodiments, the dental device may be a disposable device that may be thrown out after one or more uses.

Figure 15:
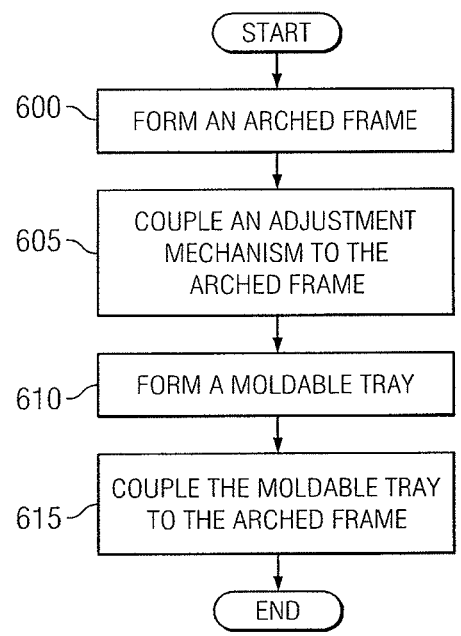
FIG. 15 illustrates an example process for creating a dental device.

FIG. 15 illustrates an example process for creating a dental device. At step 600, an arched frame is formed. In particular embodiments, the arched frame may be configured to be positioned proximate to the occlusal surface of a user's dental arch such that the arched frame extends beyond the cuspids of the user's dental arch. The arched frame may define a plurality of apertures. At step 605, an adjustment mechanism is coupled to the arched frame. In particular embodiments, the adjustment mechanism may comprise a hook and a threaded adjustor. At step 610, a moldable tray is formed. In particular embodiments, the moldable tray may comprise a channel configured to engage at least some of the teeth of the user's dental arch. In some embodiments, the channel may be shaped to conform to the teeth of a generic user's dental arch. In other embodiments, the channel may be a smooth channel configured to cover some of the teeth of the user's dental arch. In particular embodiments, the channel may be further shaped to conform to a particular user's dental arch. At step 615, the moldable tray is coupled to the arched frame. In particular embodiments, the moldable tray may engage the plurality of apertures. In particular embodiments the process may be repeated to form a second arched frame and a second moldable tray. In particular embodiments, the arched frame may comprise kevlar polycarbon, acryllic, polycarbonate resin thermoplastic, or any other suitable hard plastic polymer. In particular embodiments, the moldable tray may comprise polycaprolactone.

In particular embodiments, the process illustrated in FIG. 15 may lead to faster creation and production of dental devices. Users may avoid sending dental impressions to a laboratory to create a dental devices thus saving time and money.

Although example steps are illustrated and described, the present invention contemplates two or more steps taking place substantially simultaneously or in a different order. For example, step 605, coupling an adjustment mechanism to the arched frame, may be performed after step 610, forming a moldable tray. In addition, the present invention contemplates using methods with additional steps, fewer steps, or different steps, so long as the steps remain appropriate for creating a dental device.

Although the present invention has been described above in connection with several embodiments, changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A dental device comprising:
   an arched frame configured to be positioned proximate to the occlusal surface of a user's dental arch, such that the arched frame extends beyond the cuspids of the user's dental arch, the arched frame defining a plurality of apertures, and the arched frame comprising an adjustment mechanism; and
   a moldable tray coupled to the arched frame and engaging the plurality of apertures, the moldable tray comprising a channel configured to engage at least some of the teeth of the user's dental arch;
   wherein the moldable tray extends beyond a labial edge of the arched frame in the labial direction.

2. The dental device of claim 1 wherein the adjustment mechanism comprises a hook and a threaded adjustor.

3. The dental device of claim 2 further comprising:
   a second arched frame configured to be positioned proximate to the occlusal surface of the user's second dental arch, such that the second arched frame extends beyond the cuspids of the user's second dental arch, the second arched frame defining a second plurality of apertures, and the second arched frame comprising a receiving mechanism coupled to the lingual portion of the second arched frame; and
   a second moldable tray coupled to the second arched frame and engaging the second plurality of apertures, the second moldable tray comprising a second channel configured to engage at least some of the teeth of the user's second dental arch.

4. The dental device of claim 3 wherein the hook is configured to engage the receiving mechanism.

5. The dental device of claim 4 wherein the threaded adjustor is configured to adjust the forward position of the arched frame relative to the second arched frame.

6. The dental device of claim 3 wherein the user's dental arch is a maxillary arch and the user's second dental arch is a mandibular arch.

7. The dental device of claim 1 wherein the arched frame comprises polycarbonate resin thermoplastic.

8. The dental device of claim 1 wherein the moldable tray comprises polycaprolactone.

9. A dental device comprising:
   an arched frame configured to be positioned proximate to the occlusal surface of a user's maxillary arch, such that the arched frame extends beyond the cuspids of the user's maxillary arch, the arched frame defining a plurality of apertures, and the arched frame comprising an adjustment mechanism, the adjustment mechanism comprising a hook and a threaded adjustor;
   a moldable tray coupled to the arched frame and engaging the plurality of apertures, the moldable tray comprising a channel configured to engage at least some of the teeth of the user's maxillary arch, wherein the moldable tray extends beyond a labial edge of the arched frame in the labial direction;
   a second arched frame configured to be positioned proximate to the occlusal surface of the user's mandibular arch, such that the second arched frame extends beyond the cuspids of the user's mandibular arch, the second arched frame defining a second plurality of apertures, and the second arched frame comprising a receiving mechanism coupled to the lingual portion of the second arched frame; and
   a second moldable tray coupled to the second arched frame and engaging the second plurality of apertures, the second moldable tray comprising a second channel configured to engage at least some of the teeth of the user's mandibular arch,
   wherein the hook is configured to engage the receiving mechanism and wherein the threaded adjustor is configured to adjust the forward position of the arched frame relative to the second arched frame.

10. A method of forming a dental device comprising:
    forming an arched frame configured to be positioned proximate to the occlusal surface of a user's dental arch, such that the arched frame extends beyond the cuspids of the user's dental arch, the arched frame defining a plurality of apertures;
    coupling an adjustment mechanism to the arched frame;
    forming a moldable tray, the moldable tray comprising a channel configured to engage at least some of the teeth of the user's dental arch; and
    coupling the moldable tray to the arched frame such that the moldable tray extends beyond a labial edge of the arched frame in the labial direction, the moldable tray engaging the plurality of apertures.

11. The method of claim 10 wherein the adjustment mechanism comprises a hook and a threaded adjustor.

12. The method of claim 11 further comprising the steps of:
    forming a second arched frame configured to be positioned proximate to the occlusal surface of the user's second dental arch, such that the second arched frame extends beyond the cuspids of the user's second dental arch, the second arched frame defining a second plurality of apertures, and the second arched frame comprising a receiving mechanism coupled to the lingual portion of the second arched frame;
    forming a second moldable tray, the second moldable tray comprising a second channel configured to engage at least some of the teeth of the user's second dental arch; and
    coupling the second moldable tray to the second arched frame, the second moldable tray engaging the second plurality of apertures.

13. The method of claim 12 wherein the hook is configured to engage the receiving mechanism.

14. The method of claim 13 wherein the threaded adjustor is configured to adjust the forward position of the arched frame relative to the second arched frame.

15. The method of claim 12 wherein the user's dental arch is a maxillary arch and the user's second dental arch is a mandibular arch.

16. The method of claim 10 wherein the arched frame comprises polycarbonate resin thermoplastic.

17. The method of claim 10 wherein the moldable tray comprises polycaprolactone.

18. A method of forming a dental device comprising:
    forming an arched frame configured to be positioned proximate to the occlusal surface of a user's maxillary arch, such that the arched frame extends beyond the cuspids of the user's maxillary arch, the arched frame defining a plurality of apertures;
    coupling an adjustment mechanism to the arched frame, the adjustment mechanism comprising a hook and a threaded adjustor;

forming a moldable tray, the moldable tray comprising a channel configured to engage at least some of the teeth of the user's maxillary arch;

coupling the moldable tray to the arched frame such that the moldable tray extends beyond a labial edge of the arched frame in the labial direction, the moldable tray engaging the plurality of apertures;

forming a second arched frame configured to be positioned proximate to the occlusal surface of the user's mandibular arch, such that the second arched frame extends beyond the cuspids of the user's mandibular arch, the second arched frame defining a second plurality of apertures;

coupling a receiving mechanism to the lingual portion of the second arched frame;

forming a second moldable tray, the second moldable tray comprising a second channel configured to engage at least some of the teeth of the user's mandibular arch; and coupling the second moldable tray to the second arched frame, the second moldable tray engaging the second plurality of apertures, wherein the hook is configured to engage the receiving mechanism and wherein the threaded adjustor is configured to adjust the forward position of the arched frame relative to the second arched frame.

* * * * *